US009642555B2

(12) United States Patent
Bonner et al.

(10) Patent No.: US 9,642,555 B2
(45) Date of Patent: May 9, 2017

(54) SUBCUTANEOUS LEAD GUIDANCE

(75) Inventors: Matthew Bonner, Plymouth, MN (US);
Kenneth Gardeski, Plymouth, MN (US); Bruce R. Mehdizadeh, Savage, MN (US); Roger Christopherson, Vadnais Heights, MN (US); Michael R. Neidert, County Galway (IE)

(73) Assignee: Medtronic, Inc., Minneapolis, MN (US)

( * ) Notice: Subject to any disclaimer, the term of this patent is extended or adjusted under 35 U.S.C. 154(b) by 1438 days.

(21) Appl. No.: 12/503,298

(22) Filed: Jul. 15, 2009

(65) Prior Publication Data
US 2010/0125194 A1    May 20, 2010

Related U.S. Application Data

(60) Provisional application No. 61/116,492, filed on Nov. 20, 2008.

(51) Int. Cl.
*A61B 5/05*    (2006.01)
*A61B 5/06*    (2006.01)
(Continued)

(52) U.S. Cl.
CPC .............. *A61B 5/06* (2013.01); *A61B 5/0538* (2013.01); *A61B 34/20* (2016.02); *A61M 25/02* (2013.01);
(Continued)

(58) Field of Classification Search
CPC ......... A61B 5/06; A61B 34/20; A61B 5/0538; A61B 2034/2051; A61B 2034/2072;
(Continued)

(56) References Cited

U.S. PATENT DOCUMENTS 5,342,407 A    8/1994    Dahl et al.
5,468,229 A    11/1995    Chandler
(Continued)

FOREIGN PATENT DOCUMENTS

EP        1 743 591 A2    1/2007
WO    WO-02053225 A2    7/2002
WO    WO-2004047919 A2    6/2004

OTHER PUBLICATIONS (PCT/US2010/034834) PCT Notification of Transmittal of the International Search Report and the Written Opinion of the International Searching Authority.

*Primary Examiner* — Jonathan Cwern
(74) *Attorney, Agent, or Firm* — Carol F. Barry

(57) ABSTRACT

An apparatus for subcutaneous lead guidance includes a flexible guide strap, a navigation catheter and a tunneling tool. The guide strap includes an upper layer having a plurality of retainer formations and a substrate attachable on a patient's skin extending between an incision and a target site. The navigation catheter is coupled to the upper layer via the retainer formations from a first end to a second end of the guide strap. The navigation catheter includes a plurality of position sensors for generating a subcutaneous navigation volume between the incision and the target site when the navigation catheter is coupled to a navigation system. The tunneling tool has a distal portion with a leading end and at least one position sensor on the distal portion for viewing digital representation of the distal portion in relation to the navigation volume on a display coupled to the navigation system.

7 Claims, 19 Drawing Sheets

(51) Int. Cl.
*A61B 5/053* (2006.01)
*A61M 25/02* (2006.01)
*A61B 17/00* (2006.01)
*A61M 25/01* (2006.01)
*A61B 34/20* (2016.01)

(52) U.S. Cl.
CPC ............ *A61B 2017/00243* (2013.01); *A61B 2034/2051* (2016.02); *A61B 2034/2072* (2016.02); *A61M 25/0194* (2013.01); *A61M 2025/0166* (2013.01); *A61M 2025/026* (2013.01)

(58) Field of Classification Search
CPC ........ A61B 2017/00243; A61M 25/02; A61M 25/0194; A61M 2025/0166; A61M 2025/026
USPC ........................................... 600/424
See application file for complete search history.

(56) References Cited

U.S. PATENT DOCUMENTS

| | | | |
|---|---|---|---|
| 5,496,282 A | 3/1996 | Militzer | |
| 5,592,939 A | 1/1997 | Martinelli | |
| 5,782,841 A | 7/1998 | Ritz et al. | |
| 5,913,820 A | 6/1999 | Bladen et al. | |
| 5,983,126 A | 11/1999 | Wittkampf | |
| 5,987,352 A | 11/1999 | Klein et al. | |
| 6,200,265 B1 | 3/2001 | Walsh et al. | |
| 6,314,310 B1 | 11/2001 | Ben-Haim et al. | |
| 6,381,485 B1 | 4/2002 | Hunter et al. | |
| 6,618,612 B1 | 9/2003 | Acker | |
| 6,636,757 B1 | 10/2003 | Jascob et al. | |
| 6,671,554 B2 | 12/2003 | Gibson et al. | |
| 6,741,883 B2 * | 5/2004 | Gildenberg | 600/429 |
| 7,383,085 B2 | 6/2008 | Olson | |
| 7,389,138 B2 | 6/2008 | Wagner et al. | |
| 2004/0097805 A1 | 5/2004 | Verard et al. | |
| 2004/0097806 A1 | 5/2004 | Hunter et al. | |
| 2004/0199072 A1 * | 10/2004 | Sprouse et al. | 600/424 |
| 2004/0215071 A1 | 10/2004 | Frank et al. | |
| 2006/0025677 A1 | 2/2006 | Verard et al. | |
| 2007/0016089 A1 | 1/2007 | Fischell et al. | |
| 2007/0164900 A1 | 7/2007 | Schneider et al. | |
| 2008/0039738 A1 | 2/2008 | Dinsmoor et al. | |
| 2008/0132969 A1 * | 6/2008 | Bennett et al. | 607/41 |
| 2008/0171937 A1 | 7/2008 | Dukesherer et al. | |
| 2008/0208247 A1 | 8/2008 | Rutten et al. | |
| 2008/0208248 A1 | 8/2008 | Rutten et al. | |
| 2008/0208303 A1 | 8/2008 | Rutten et al. | |
| 2008/0208339 A1 | 8/2008 | Rutten et al. | |
| 2008/0300481 A1 | 12/2008 | Groszmann | |
| 2008/0319311 A1 | 12/2008 | Hamadeh | |
| 2009/0036917 A1 | 2/2009 | Anderson | |
| 2009/0088805 A1 | 4/2009 | Leyden et al. | |
| 2009/0088806 A1 | 4/2009 | Leyden et al. | |

\* cited by examiner

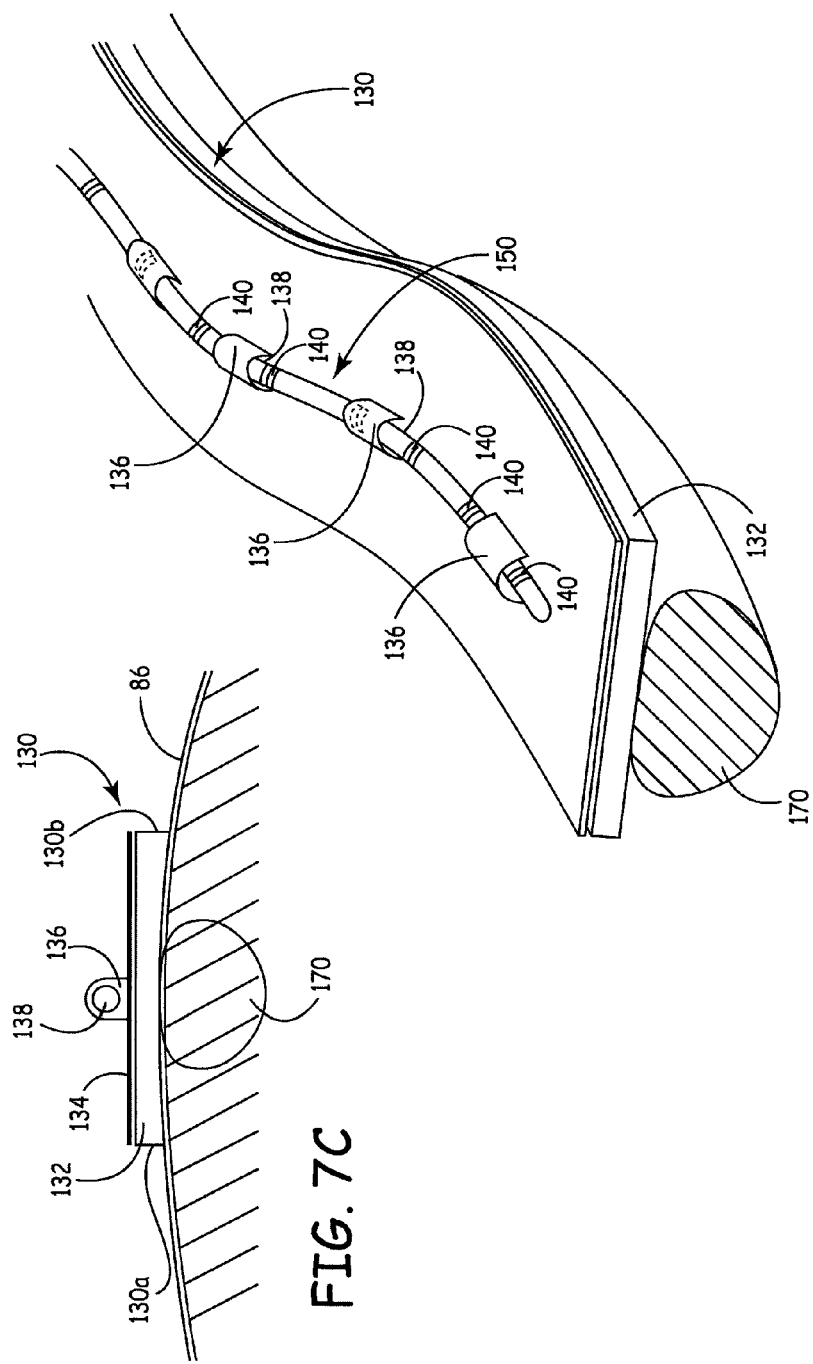

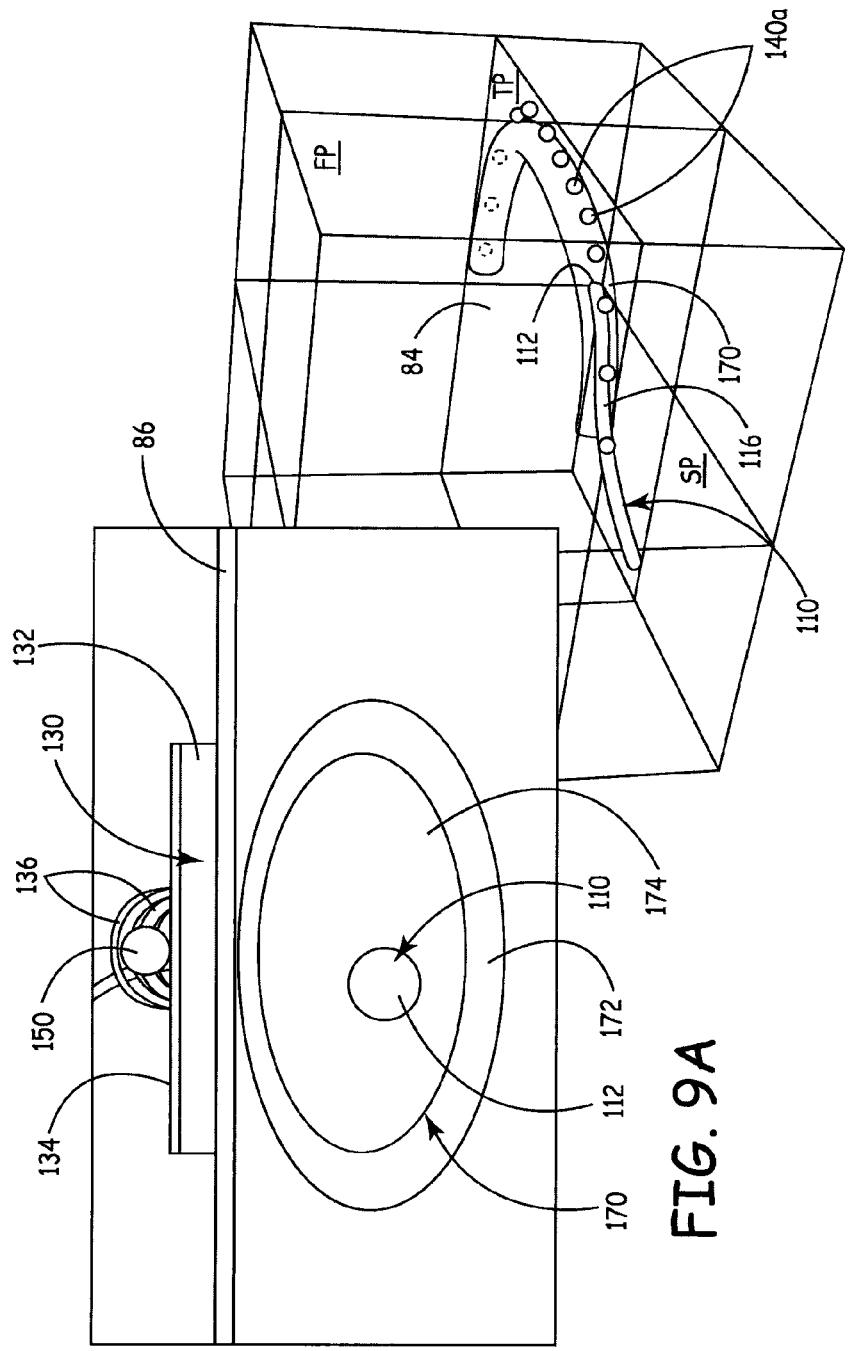

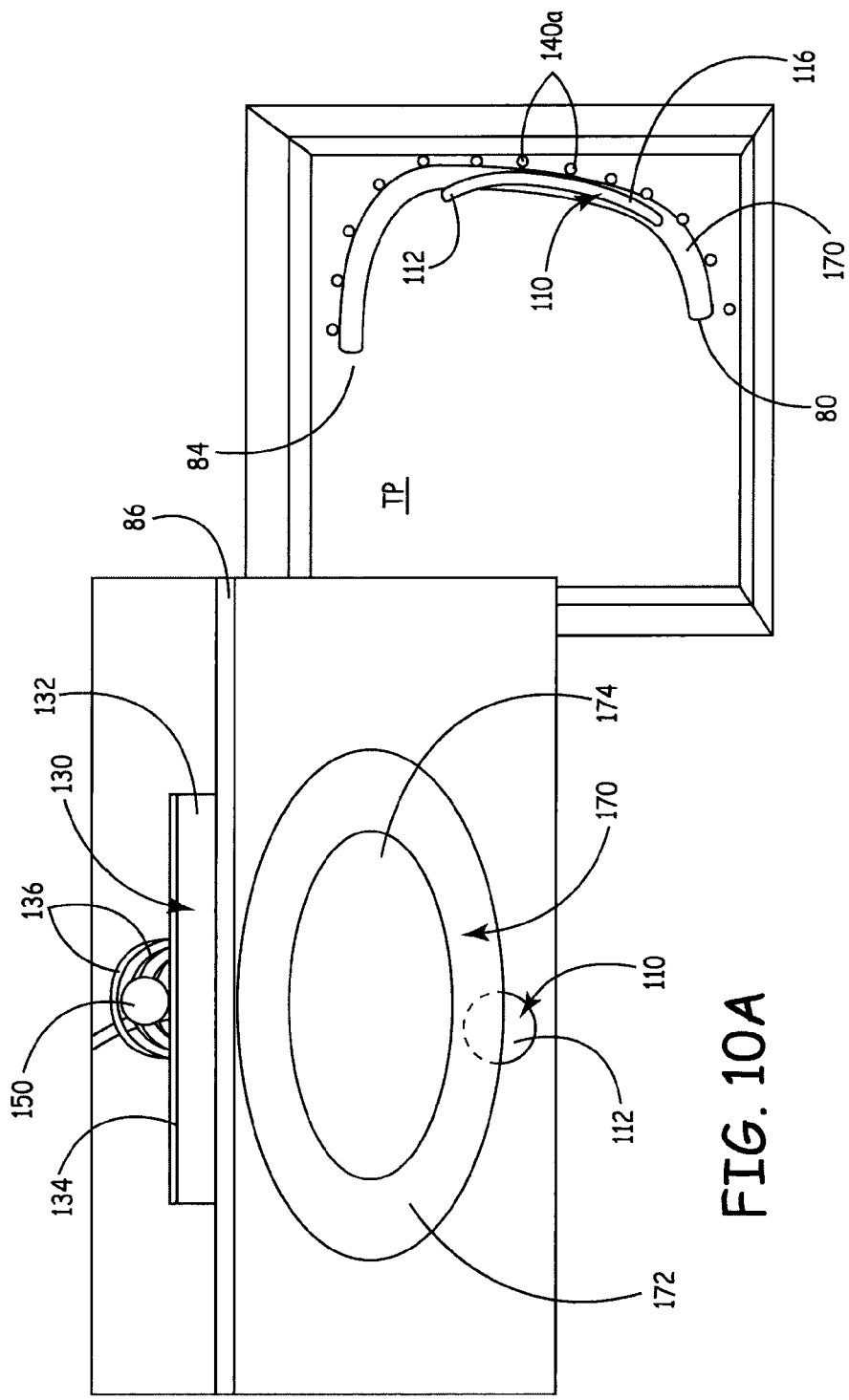

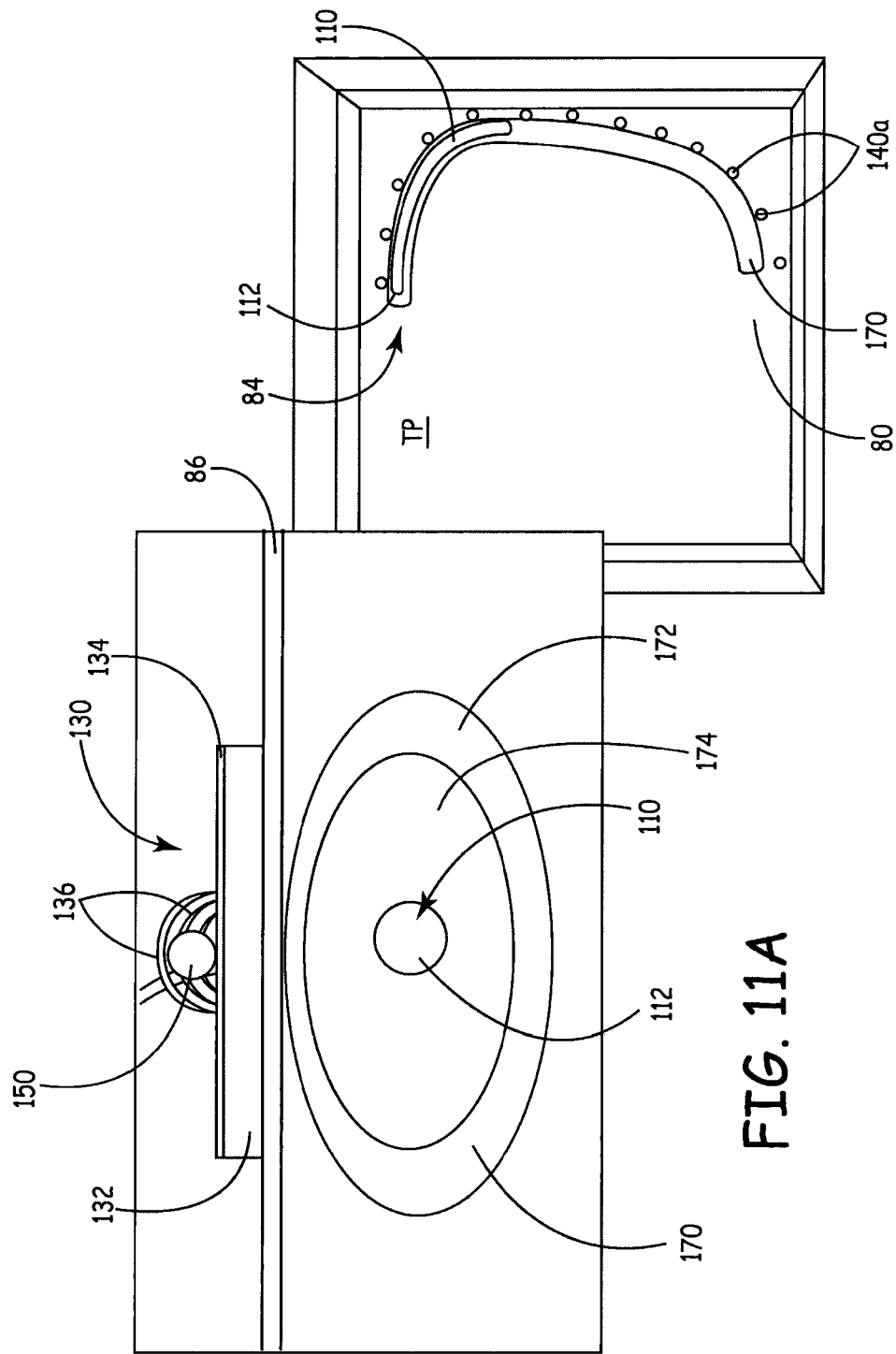

SUBCUTANEOUS LEAD GUIDANCE

CROSS-REFERENCE TO RELATED APPLICATIONS

This application claims the benefit of U.S. Provisional Application No. 61/116,492, filed on Nov. 20, 2008. The disclosure of this application is incorporated herein by reference.

INTRODUCTION

Many types of implantable medical devices are implanted into patient's bodies to deliver cardioversion and/or defibrillation shocks to a patient's heart when a malignant tachyarrhythmia, e.g., atrial or ventricular fibrillation, is detected. Current cardioverter-defibrillators can also include right and left heart chamber pacing capabilities for improving the cardiac output of patient's hearts that are in heart failure, and are generally referenced as implantable cardioverter-defibrillators (ICDs).

Various fluoroscopic and other real-time image systems methods are used for the implantation of leads associated with the ICDs. The present teachings provide a system for tracking the position of a lead for an ICD during subcutaneous implantation without the use of fluoroscopy. The present teachings can also be applied with subcutaneous implantation of Insertable Cardiac Monitors (ICMs) for Acute Myocardial Infraction (AMI) in which a lead is tunneled from the ICM to the side of the thorax opposite to the ICM.

SUMMARY

The present teachings provide in various embodiments an apparatus for subcutaneous lead guidance includes a flexible guide strap, a navigation catheter and a tunneling tool. The guide strap includes an upper layer having a plurality of retainer formations and a substrate attachable on a patient's skin extending between an incision and a target site. The navigation catheter is coupled to the upper layer via the retainer formations from a first end to a second end of the guide strap. The navigation catheter includes a plurality of position sensors for generating a subcutaneous navigation volume between the incision and the target site when the navigation catheter is coupled to a navigation system. The tunneling tool has a distal portion with a leading end and at least one position sensor on the distal portion for viewing digital representation of the distal portion in relation to the navigation volume on a display coupled to the navigation system.

The present teachings provide a method for subcutaneous lead guidance. The method includes comprising attaching a substrate of flexible guide strap on a patient's skin between an incision and a target site, wherein the guide strap has a plurality of hoops coupled to an upper layer of the guide strap. The method includes passing navigation catheter having a plurality of position sensors through the plurality of hoops, and operably coupling the navigation catheter to a navigation system. The method also includes generating a subcutaneous navigation volume between the incision and the target site, viewing a digital representation of the subcutaneous navigation volume on a display of the navigation system, and guiding a tunneling tool subcutaneously through the incision to the target site without fluoroscopic assistance. The tunneling tool has at least one position sensor coupled to a distal portion of the tunneling tool. The method includes viewing a digital representation of the distal portion of the tunneling tool in relation to the navigation volume on the display; and maintaining the leading end of the tunneling tool within the navigation volume.

In various embodiments, the present teachings provide an apparatus for subcutaneous lead guidance. The apparatus includes a flexible guide strap having a first end and a second end. The guide strap can be attached on a patient's skin and extending between an incision and a target site. The apparatus includes a shielded flexible circuit and a plurality of position sensors such as, for example, induction coils attached to the guide strap and operably coupled to a connector for generating a subcutaneous navigation volume between the incision and the target site when the connector is operably coupled to a navigation system. The apparatus includes a tunneling tool having a distal portion with a leading end and at least one position sensor on the distal portion for viewing digital representation of the distal portion in relation to the navigation volume on a display coupled to the navigation system.

In various embodiments, the present teachings provide a method for subcutaneous lead guidance that includes attaching a substrate of a flexible guide strap on a patient's skin between an incision and a target site. The guide strap includes a shielded flexible circuit with plurality of position sensors such as, for example, induction coils operably coupled to a navigation system. The method includes generating a subcutaneous navigation volume between the incision and the target site, and viewing a digital representation of the subcutaneous navigation volume on a display of the navigation system. The method includes guiding a tunneling tool subcutaneously through the incision to the target site without fluoroscopic assistance, wherein the tunneling tool has at least one position sensor coupled to a distal portion of the tunneling tool. The method includes viewing a digital representation of the distal portion of the tunneling tool in relation to the navigation volume on the display, and maintaining a leading end of the tunneling tool within the navigation volume.

In various embodiments, the method for subcutaneous lead guidance includes attaching a substrate of a flexible guide strap on a patient's skin between an incision and a target site, attaching a first electrode on a distal portion of a tunneling tool, the tunneling tool having a leading end, and attaching at least one second electrode on the guide strap at the target site. The method includes operably coupling the first and second electrodes to an induction-based feedback system via electrical cable, generating an alert signal indicative of the distance between the leading end of the tunneling tool and the target site, and guiding the tunneling tool subcutaneously through the incision to the target site without fluoroscopic assistance based on the alert signal.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 7C is an environmental sectional view of the guide strap according to the present teachings;

FIG. 7D is an environmental perspective view of the navigation catheter and guide strap of FIG. 7A according to the present teachings;

FIG. 9A is a representative screen image illustrating digital representations of a cross-sectional view of the navigation volume and the leading end of the tunneling tool for subcutaneous lead delivery according to the present teachings;

FIG. 9B is a representative screen image illustrating digital representations of a perspective view of the navigation volume and a distal portion of the tunneling tool relative to a transverse plane for subcutaneous lead delivery according to the present teachings;

FIG. 10A is a representative screen image illustrating digital representations of a cross-sectional view of the navigation volume with the leading end of the tunneling tool veering away from the navigation volume;

FIG. 10B is a representative screen image illustrating digital representations of a perspective view of the navigation volume and a distal portion of the tunneling tool veering away from the navigation volume;

FIG. 11A is a representative screen image illustrating digital representations of a cross-sectional view of the navigation volume with the leading end of the tunneling tool centered in the navigation volume at the target site;

FIG. 11B is a representative screen image illustrating digital representations of a perspective view of the navigation volume with the leading end of the tunneling tool centered in the navigation volume at the target site;

DESCRIPTION OF VARIOUS EMBODIMENTS

Figure 1:
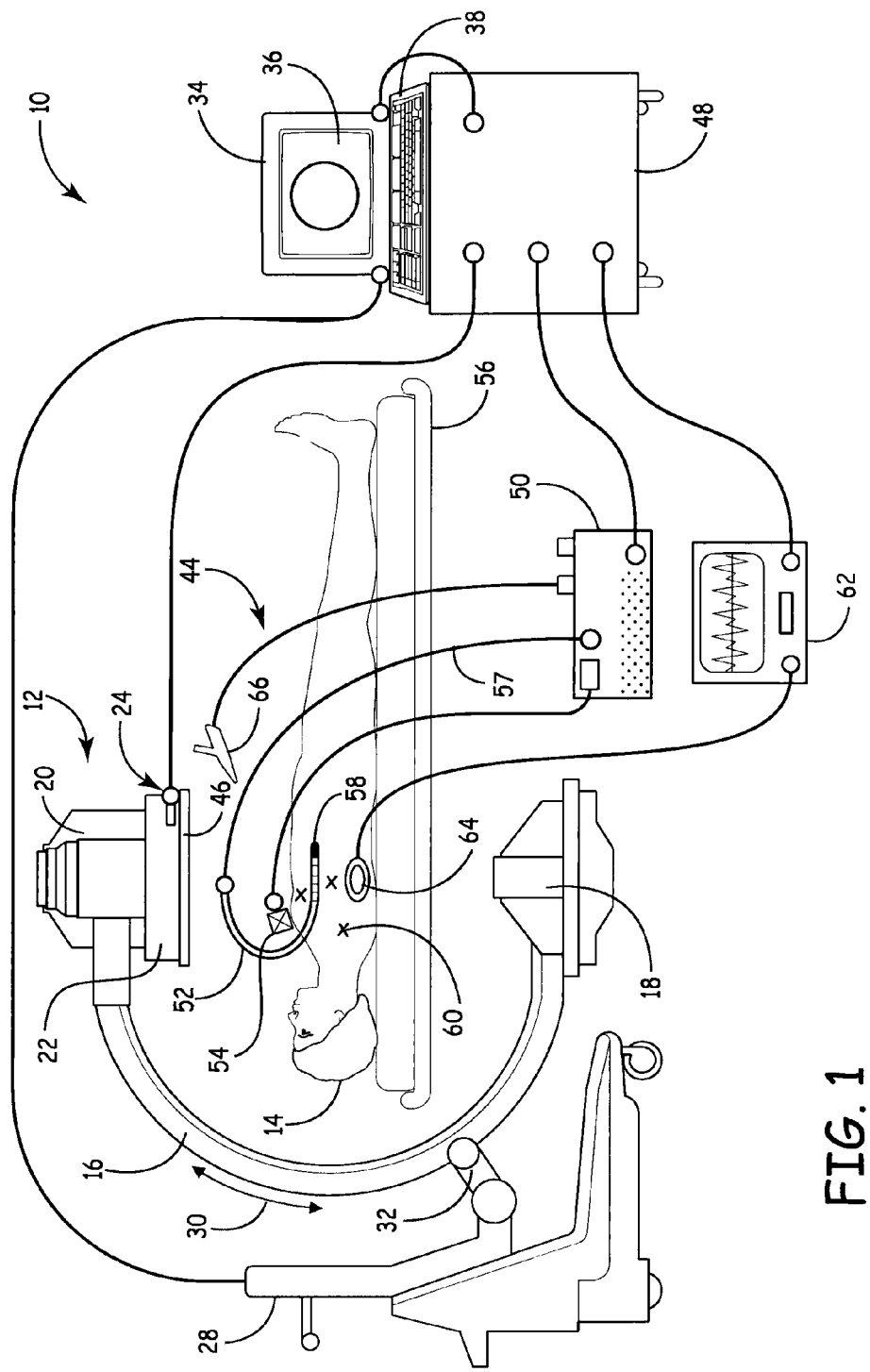
FIG. 1 is a diagram of an exemplary catheter navigation system.

The following description is merely exemplary in nature and is in no way intended to limit the present teachings, applications, or uses. Although the present teachings are described in connection with defibrillations systems, and in particular in connection with implantable cardioverter-defibrillators (ICDs), the present teachings are also applicable to subcutaneous delivery of leads for other medical devices, including insertable/implantable cardiac monitors (ICMs) for Acute Myocardial Infraction (AMI), in which a lead is tunneled from the ICM to the side of the thorax opposite to the ICM.

Exemplary defibrillation systems can include, for example, a pair of leads connecting the ICD to defibrillation electrodes that are implanted subcutaneously outside of the rib cage in the thoracic region on opposite sides of the heart. More particularly, one defibrillation electrode can be subcutaneously implanted to the left of, and anterior with respect to, the heart, and the other defibrillation electrode can be subcutaneously implanted posterior with respect to the heart, and to the right of the heart. The ICD can also implanted anterior and to the left of heart, below one of the subcutaneous defibrillation electrodes. The ICD can incorporate circuitry for sensing cardiac electrical activity. The same subcutaneous defibrillation electrodes can be used for sensing such activity as well as delivering defibrillation pulses.

In various embodiments, the ICD can include first and second hermetically sealed housings in which the components of the ICD are distributed for reducing the bulk of a single housing ICD, as disclosed in commonly assigned U.S. Pat. No. 7,383,085 ('085), the disclosure of which is incorporated herein by reference. The first and second housings can be tethered together with a connecting element, such as an electrical cable. The ICD of '085 can be implanted by making at least one surgical incision into subcutaneous space between the patient's skin and ribcage, inserting the first hermetically sealed housing through the incision and advancing the first hermetically sealed housing subcutaneously to a first subcutaneous implantation site, inserting the second hermetically sealed housing through the incision and advancing the second hermetically sealed housing subcutaneously to a second subcutaneous implantation site spaced from the first subcutaneous implantation site so that the electrical cable is disposed subcutaneously between the first and second hermetically sealed housings, and closing the incision.

In various embodiments, the implantation method can include making two surgical incisions into subcutaneous or submuscular space and inserting the two components of the ICD into each one of the incisions. The connective element is then tunneled between the two incisions to provide connection between the two component parts.

The connecting electrical cable between the first and second component of the ICD can installed using a tunneling tool that is already inserted into the lumen of the electrode at the distal end and includes a blunt dissection tip. Various tunneling tools can be used, such as the tunneling tool Model 6996T, commercially available from Medtronic, Inc., Minneapolis, Minn. or the tunneling tool disclosed in commonly assigned U.S. Pat. No. 5,782,841 or in commonly-assigned and co-pending U.S. patent application Ser. No. 12/250,670, filed on Oct. 14, 2008. The disclosures of U.S. Pat. No. 5,782,841 and U.S. patent application Ser. No. 12/250,670 are incorporated herein by reference.

Exemplary Insertable Cardiac Monitors (ICMs) can include, for example, ICM similar to the Reveal® XT or DX ICMs commercially available from Medtronic, Inc. Minneapolis, Minn. Although the Reveal® devices may be used without leads for monitoring cardiac arrhythmias, Reveal®-like ICMs can be used for Acute Myocardial Infraction (AMI) with a lead from the ICM tunneled to the side of the thorax opposite to the ICM, as described above in connection with the ICD devices. The lead connected to the ICM provides an anterior posterior vector for detection of AMI. The anterior posterior vector can have the largest amplitude ST segment elevation for most infarct locations. Although the commercially available Reveal® ICM can be the size of a memory stick weighing about 15 grams, for AMI applications for use with the present teachings the ICM devices can be elongated elements of about one inch long and ¼ inch in diameter or smaller using miniaturized circuit technology.

The present teachings can be used in conjunction with various exemplary navigation systems, such as those described in commonly assigned U.S. Pat. No. 6,636,757, and in currently pending and commonly assigned patent application Ser. No. 10/299,969, filed Nov. 19, 2003 (2004/0097806) and Ser. No. 10/619,126, filed Jul. 14, 2003 (2004/0097805), the disclosures of each of which are incorporated herein by reference. An exemplary navigation system is described below in connection with FIGS. 1 and 1A.

FIG. 1 is a diagram illustrating an overview of an exemplary image-guided catheter navigation system 10 for use in non-line-of-site navigating of a catheter during cardiac therapy or any other soft tissue therapy, including the cell/drug delivery therapy discussed herein. It should further be noted that the navigation system 10 may be used to navigate any other type of instrument or delivery system, including guide wires, needles, drug delivery systems, cell delivery systems, gene delivery systems and biopsy systems. Moreover, these instruments may be used for cardiac therapy or any other therapy in the body or be used to navigate or map any other regions of the body, such as moving body structures. However, each region of the body poses unique requirements to navigate, as disclosed herein. For example, the navigation system 10 can address multiple cardiac, neurological, organ and other soft tissue therapies, including drug delivery, cell transplantation, gene delivery, electrophysiology ablations, transmyocardial vascularization (TMR), biopsy guidance, and virtual echography imaging.

Figure 1A:
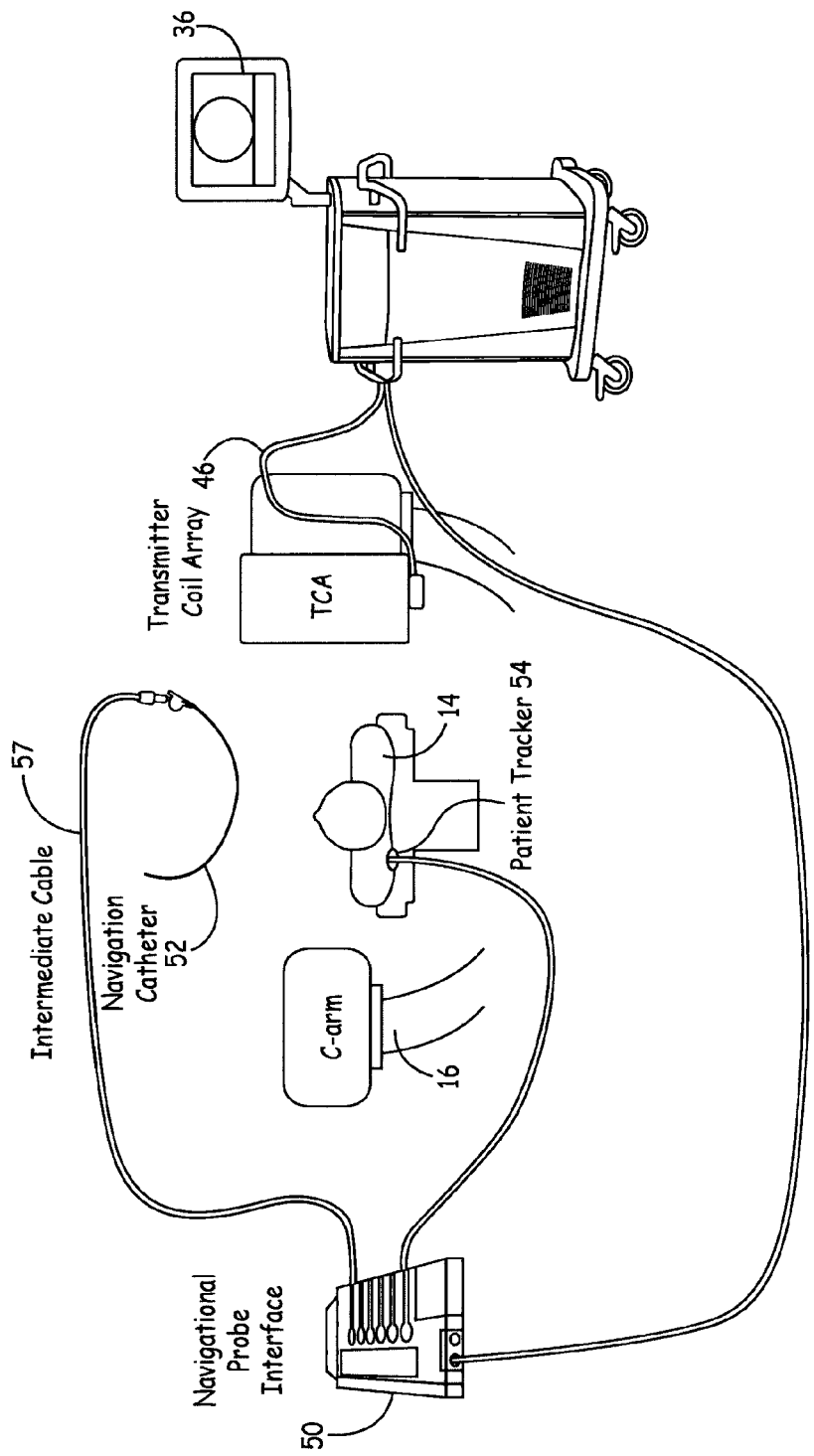
FIG. 1A is a diagram of an exemplary catheter navigation system.

Referring to FIGS. 1, and 1A, the navigation system 10 may include an imaging device 12 that is used to acquire pre-operative or real-time images of a patient 14. The imaging device 12 can be a fluoroscopic x-ray imaging device that may include a C-arm 16 having an x-ray source 18, an x-ray receiving section 20, an optional calibration and tracking target 22 and optional radiation sensors 24. The calibration and tracking target 22 can include calibration markers. A C-arm controller 28 can be used to capture the x-ray images received at the receiving section 20 and store the images for later use. The C-arm controller 28 may also control the rotation of the C-arm 16. For example, the C-arm 16 may move in the direction of arrow 30 or rotate about the long axis of the patient 14, allowing anterior or lateral views of the patient 14 to be imaged. Each of these movements involves rotation about a mechanical axis 32 of the C-arm 16. In this example, the long axis of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and an associated calibration process may be eliminated. Also, the calibration process may be eliminated or not used at all for cardiac therapies. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images taken by the imaging device 12 can be captured and stored in the C-arm controller 28. Multiple two-dimensional images taken by the imaging device 12 may also be captured and assembled to provide a larger view or image of a whole region of a patient, as opposed to being directed to only a portion of a region of the patient. These images are then forwarded from the C-arm controller 28 to a controller or work station 34 having a display 36 and a user interface 38. The work station 34 provides facilities for displaying on the display 36, saving, digitally manipulating, or printing a hard copy of the received images. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images. When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

With continued reference to FIGS. 1, and 1A, the navigation system 10 can further include an electromagnetic navigation or tracking system 44 that includes a transmitter coil array 46, the coil array controller 48, a navigation probe interface 50, a navigation or electromagnetic catheter or insert 52 or any other type of instrument and a dynamic reference frame 54. Further, it should further be noted that the entire tracking system 44 or parts of the tracking system 44 may be incorporated into the imaging device 12, including the work station 34 and radiation sensors 24. Incorporating the tracking system 44 will provide an integrated imaging and tracking system. Any combination of these components may also be incorporated into the imaging device 12, which again can include a fluoroscopic C-arm imaging device or any other appropriate imaging device.

In the exemplary illustration of FIG. 1, the transmitter coil array 46 is shown attached to the receiving section 20 of the C-arm 16. However, it should be noted that the transmitter coil array 46 may also be positioned at any other location as well. For example, the transmitter coil array 46 may be positioned at the x-ray source 18, within or atop the operating room table 56 positioned below the patient 14, on side rails associated with the table 56, or positioned on the patient 14 in proximity to the region being navigated, such as on the patient's chest. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999, and U.S. Pat. No. 5,592,939, entitled "Method and System for Navigating a Catheter Probe," issued Jan. 14, 1997, each of which are incorporated herein by reference.

The transmitter coil array 46 can be controlled or driven by the coil array controller 48. The coil array controller 48 can drive each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in sensors 58 positioned in the electromagnetic catheter 52. These induced signals from the electromagnetic catheter 52 are delivered to the navigation probe interface 50 via a connection cable 57 and subsequently forwarded to the coil array controller 48. The navigation probe interface 50 provides all the necessary electrical isolation for the navigation system 10. The navigation probe interface 50 also includes amplifiers, filters and buffers required to directly interface with the sensors 58 in electromagnetic catheter 52. Alternatively, the electromagnetic catheter 52 may employ a wireless communications channel as opposed to being coupled directly to the navigation probe interface 50.

The electromagnetic catheter 52 may be equipped with at least one, and generally multiple, localization sensors 58. The electromagnetic catheter 52 may also be a steerable catheter that includes a handle at a proximal end and the multiple location sensors 58 fixed to the catheter body and spaced axially from one another along the distal segment of the electromagnetic catheter 52. The electromagnetic catheter 52, as shown in FIG. 1, includes four localization sensors 58. The localization sensors 58 are generally formed as electromagnetic receiver coils, such that the electromagnetic field generated by the transmitter coil array 46 induces current in the electromagnetic receiver coils or sensors 58. Other electromagnetic sensors can be also used, including Giant Magnetoresistance (GMR) sensors or Hall Effect sensors, for example. The electromagnetic catheter 52 may also be equipped with one or more sensors, which are operable to sense various physiological signals. For example, the electromagnetic catheter 52 may be provided with electrodes for sensing myopotentials or action potentials. In other embodiments in which a catheter is inserted vascularly, absolute pressure sensors may also be included, as well as other electrode sensors. The electromagnetic catheter 52 may also be provided with an open lumen to allow the delivery of a medical device or pharmaceutical/cell/gene agents. For example, the electromagnetic catheter 52 may be used as a guide catheter for deploying a medical lead, such as a cardiac lead for use in cardiac pacing and/or defibrillation or tissue ablation. The open lumen may alternatively be used to locally deliver local anesthetics, other pharmaceutical agents, and cell, or genetic therapies. A representative catheter which may be used is that which is disclosed in U.S. patent application Ser. No. 10/619,216, filed Jul. 14, 2003, (2004/0097805), which is hereby incorporated by reference.

In an alternate aspect, the electromagnetic sources or generators may be located within the electromagnetic catheter 52 and one or more receiver coils may be provided externally to the patient 14, forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF and accelerometers. Additionally, in subcutaneous lead delivery applications in which a catheter is guided on a strap attached to the patient's skin, as shown in and discussed in connection within FIGS. 7A and 7B, a magnetic field tracking system can be used. For example, the skin strap can include a series of closely-spaced small magnets and the catheter can include a small magnetic filed sensor to track magnetic field strength as a distance from the strap, based, for example, on the Hall Effect. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 can also coupled to the navigation probe interface 50 to forward the information to the coil array controller 48. The dynamic reference frame 54 can be a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. It will be appreciated that the dynamic reference frame 54 operates to link the image space to the patient space and is required when importing and navigating to a pre-acquired, patient-specific medical image. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as on the patient's chest, as shown in FIG. 1 or on the patient's back. The dynamic reference frame 54 can be affixed to the patient's skin, by way of a stick-on adhesive patch. The dynamic reference frame 54 may also be removably attachable to fiducial markers 60 also positioned on the patient's body.

Alternatively, the dynamic reference frame 54 may be internally attached, for example, to the wall of the patient's heart or other soft tissue using a temporary lead that is attached directly to the heart. This provides increased accuracy since this lead will track the regional motion of the heart. Gating, as further discussed herein, will also increase the navigational accuracy of the system 10. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference. It should further be noted that multiple dynamic reference frames 54 may also be employed. For example, the navigation catheter 150 with position sensors 140, discussed below in connection with FIGS. 7A-7D, 12A and 12D, can act as a series of dynamic reference frames attached on a longitudinal member or strip. In various embodiments, an external dynamic reference frame 54 may be attached to the chest of the patient 14, as well as to the back of the patient 14. Since certain regions of the body may move more than others due to motions of the heart or the respiratory system, each dynamic reference frame 54 may be appropriately weighted to increase accuracy even further. In this regard, the dynamic reference frame 54 attached to the back may be weighted higher than the dynamic reference frame 54 attached to the chest, since the dynamic reference frame 54 attached to the back is relatively static in motion.

The catheter and navigation system 10 can further include a gating device or an ECG or electrocardiogram device 62, which is attached to the patient 14, via skin electrodes 64, and in communication with the coil array controller 48. Respiration and cardiac motion can cause movement of cardiac structures relative to the electromagnetic catheter 52, even when the electromagnetic catheter 52 has not been moved. Therefore, localization data may be acquired on a time-gated basis triggered by a physiological signal. For example, the ECG or EGM signal may be acquired from the skin electrodes 64 or from a sensing electrode included on the electromagnetic catheter 52 or from a separate reference probe. A characteristic of this signal may be used to gate or trigger image acquisition during the imaging phase with the imaging device 12. By event gating at a point in a cycle the image data and/or the navigation data, the icon of the location of the electromagnetic catheter 52 relative to the heart at the same point in the cardiac cycle may be displayed on the display 36, as discussed in co-pending and commonly assigned patent application Ser. No. 12/183,688, filed Jul. 31, 2008, the disclosure of which is incorporated herein by reference.

Figure 7A:
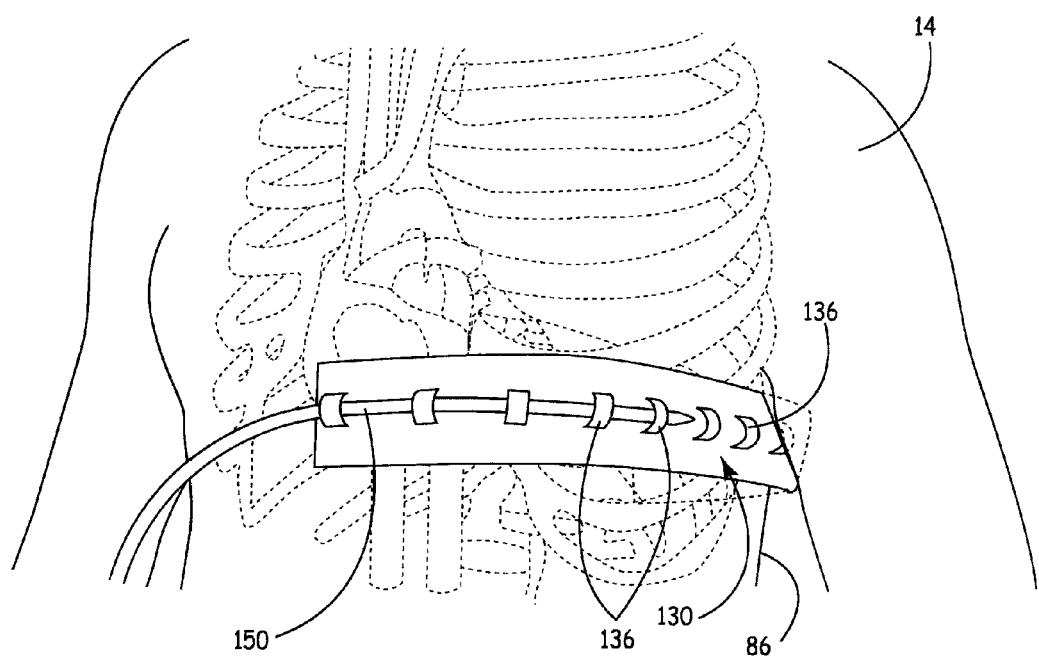
FIG. 7A is an environmental view of a navigation catheter inserted through retainers along the guide strap of FIG. 6 according to the present teachings.
Figure 7B:
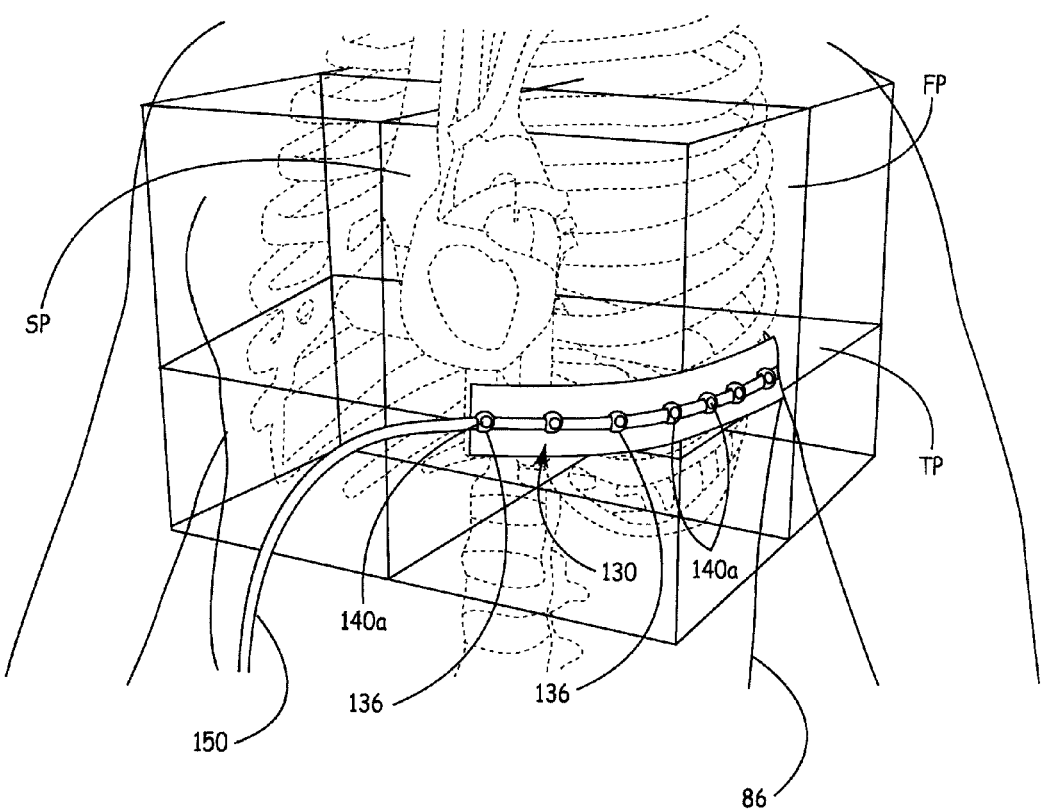
FIG. 7B is an environmental view of the navigation catheter and guide strap of FIG. 7A relative to three anatomical planes according to the present teachings.
Figure 8A:
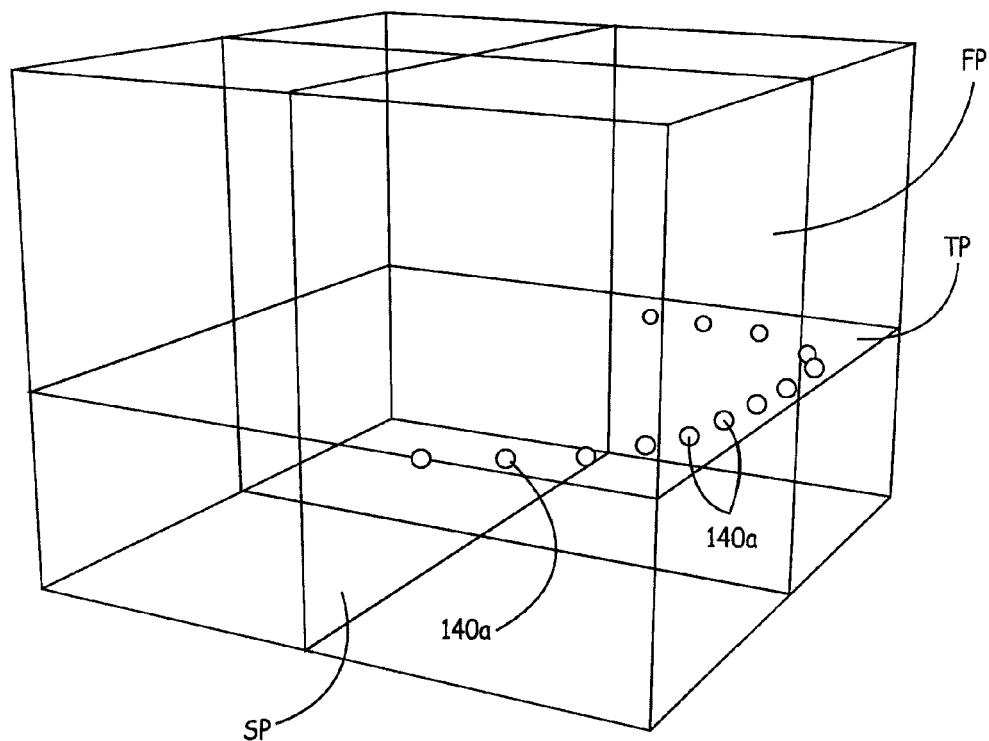
FIG. 8A is a representative screen image illustrating digital representations of the position sensors of the navigation catheter relative to a transverse plane for subcutaneous lead delivery according to the present teachings.
Figure 8B:
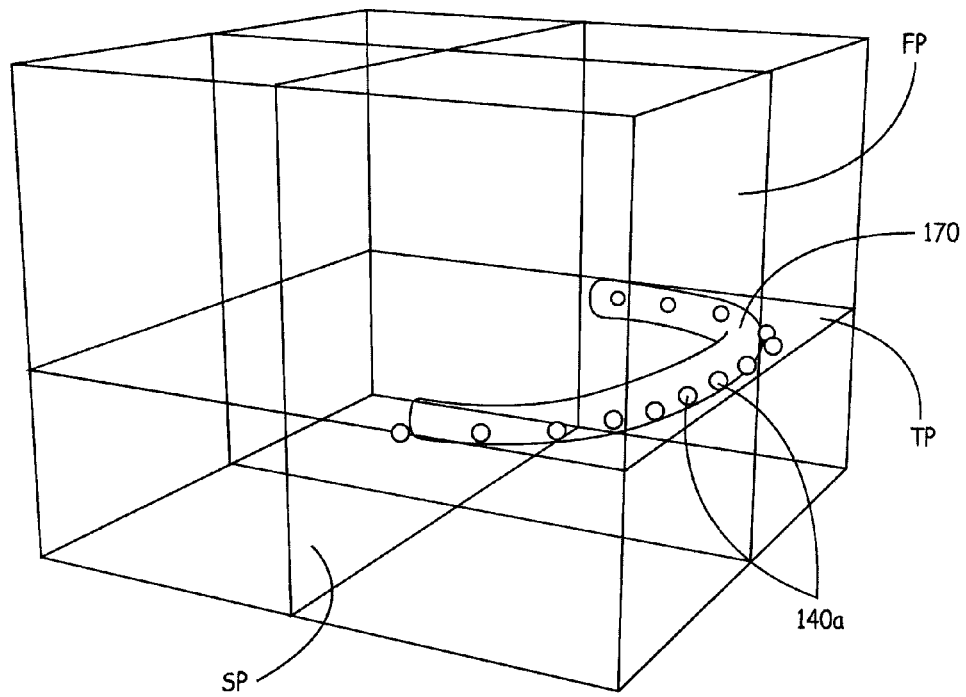
FIG. 8B is a representative screen image illustrating digital representations of the position sensors of the navigation catheter and an associated navigation volume relative to a transverse plane for subcutaneous lead delivery according to the present teachings.

Additionally or alternatively, a sensor regarding respiration may be used to trigger data collection at the same point in the respiration cycle, such as, for example, in subcutaneous lead delivery applications in which a catheter on a skin strap is tracking positions on both the anterior and posterior sides of the body, as shown in and discussed in connection within FIGS. 7A and 7B. Additional external sensors can also be coupled to the navigation system 10. These could include a capnographic sensor that monitors exhaled $CO_2$ concentration. From this, the end expiration point can be easily determined. The respiration, both ventriculated and spontaneous causes an undesirable elevation or reduction, respectively, in the baseline pressure signal. By measuring systolic and diastolic pressures at the end expiration point, the coupling of respiration noise is minimized. As an alternative to the $CO_2$ sensor, an airway pressure sensor can be used to determine end expiration.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the electromagnetic catheter 52 or pointing device is used, the work station 34, in combination with the coil array controller 48 and the C-arm controller 28, uses the translation map to identify the corresponding point on the pre-acquired image, which is exhibited on display 36. This identification is known as navigation or localization. An icon representing the localized point or an instrument is shown on the display 36 within several two-dimensional image planes, as well as on three and four dimensional images and models.

To enable image-guided navigation with real-time images of the anatomy, the navigation system 10 should be able to detect both the position of the patient's anatomy and the position of the electromagnetic catheter 52 or other surgical instrument. Knowing the location of these two items allows the navigation system 10 to compute and display the position of the electromagnetic catheter 52 in relation to the patient 14 on the radiological images. The tracking system 44 is employed to track the electromagnetic catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the electromagnetic catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the electromagnetic catheter 52 during localization and relates this spatial information to patient registration data to enable image guidance of the electromagnetic catheter 52 within the patient 14.

Patient registration is the process of determining how to correlate the position of the instrument or electromagnetic catheter 52 on the patient 14 to the position on the diagnostic or pre-acquired images. To register the patient 14, the physician or user may use point registration by selecting and storing particular points from the pre-acquired images and then touching the corresponding points on the patient's anatomy with a pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial arrays or landmarks or fiducial markers 60. Again, the landmarks or fiducial markers 60 are identifiable on the images and identifiable and accessible on the patient 14. The fiducial markers 60 can be artificial landmarks that are positioned on the patient 14 or anatomical landmarks that can be easily identified in the image data. The system 10 may also perform registration using anatomic surface information or path information, further discussed herein. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, as set forth in currently pending and co-owned U.S. patent application Ser. No. 10/644,680 filed Aug. 20, 2003 (2004/0215071), entitled "Method and Apparatus for Performing 2D to 3D Registration," which is incorporated herein by reference. The registration process may also be synched to an anatomical function, for example, by the use of the ECG device 62.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking system 44 to register and track the anatomy. Because the dynamic reference frame 54 is attached to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

Although the navigation system 10 described above is shown with a fluoroscopic imaging device 12, various embodiments of the subcutaneous lead delivery apparatus and the methods of the present teachings do not make use of fluoroscopy for the subcutaneous lead delivery, although fluoroscopy can be available for use of other related procedures, as needed. Additionally, the subcutaneous lead delivery apparatus and the method of the present teachings do not require registration between patient space and image space, although such registration can be effected in the navigation system 10, as described above, for other related procedures and uses during the surgical operation.

Figure 2:
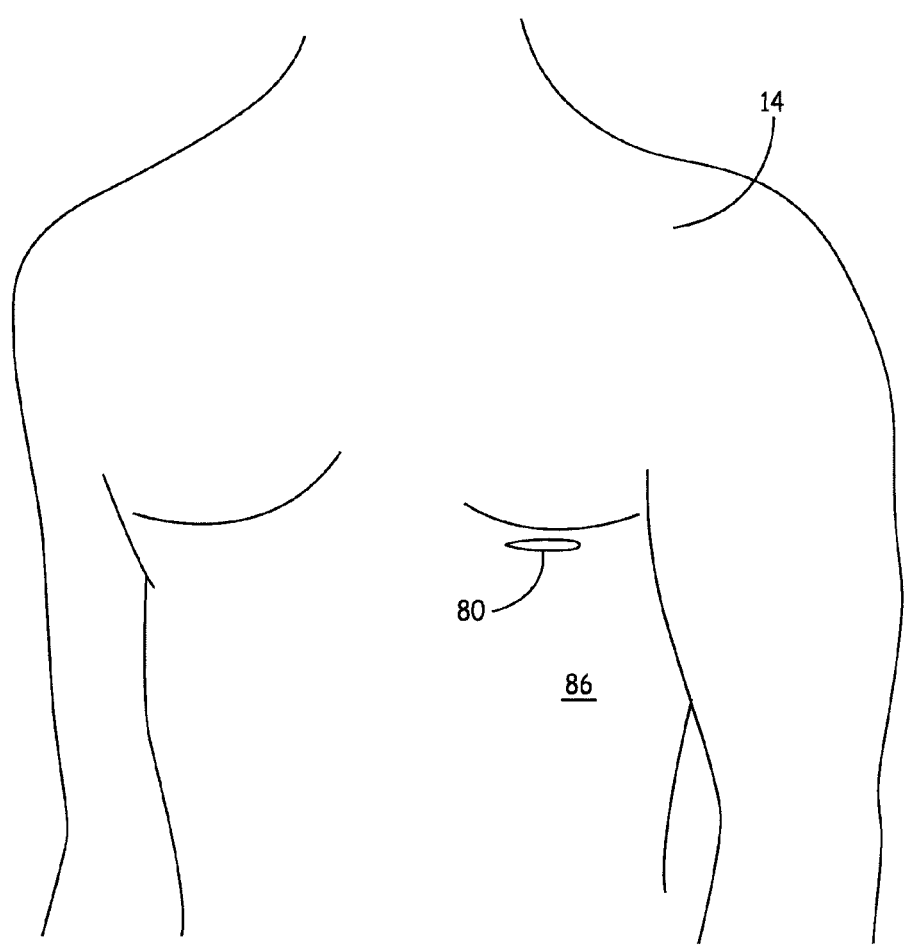
FIG. 2 is an illustration of a pectoral incision on a patient.
Figure 2A:
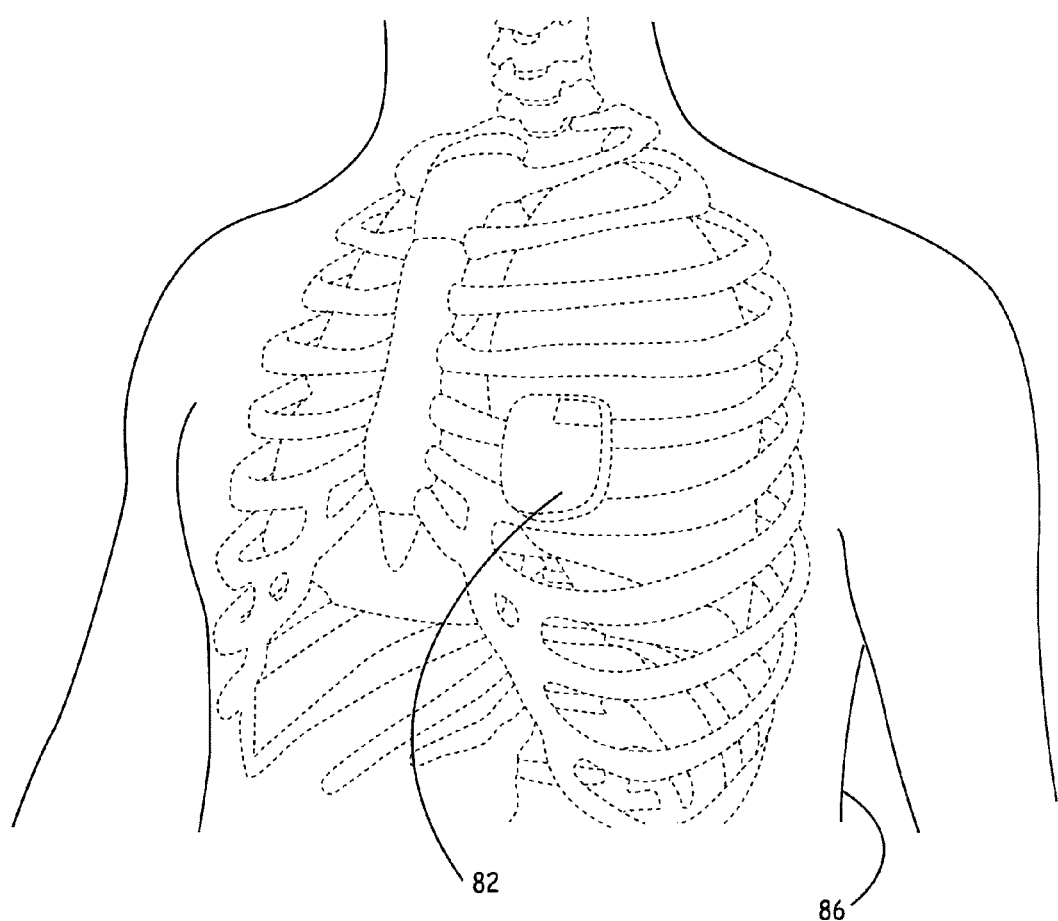
FIG. 2A is an environmental perspective view of an implantable medical device inserted through the incision of FIG. 2.
Figure 3:
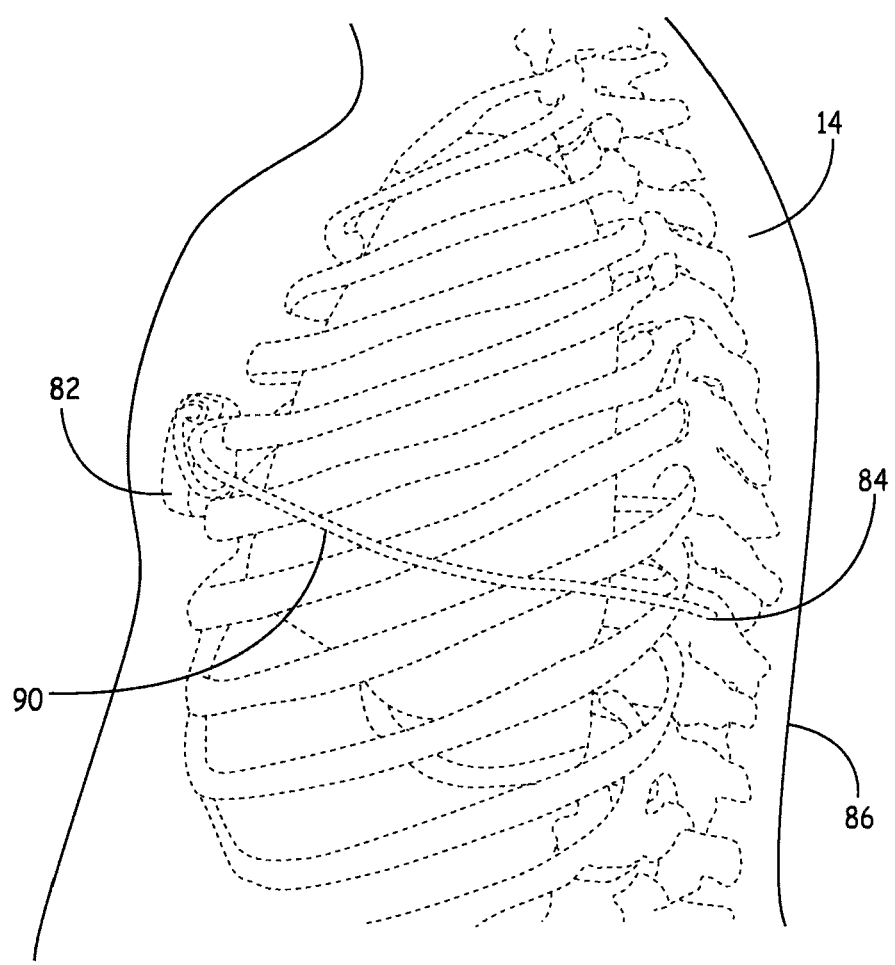
FIG. 3 is an environmental perspective view of a path of an electrical lead extending from the implantable medical device to a posterior target site.

FIGS. 2, 2A, and 3 illustrate an exemplary anterior or pectoral incision 80 for implanting an ICD or ICM or other implantable device 82, and an electrically conductive medical lead 90 to be delivered subcutaneously for electrical connection with the implantable device 82. Upon implantation, the lead 90 can extend from implantable device 82 to a target location 84. In the exemplary illustration of FIG. 3, the lead 90 extends from an anterior position to a posterior position of the patient 14, but other incision and target locations can be used, For example, the incision 80 can be placed laterally relative to the patient 14, two incisions can be used, etc. The subcutaneous delivery system and method described herein can be used regardless of the location of the implantable device 82, incision(s) 80 and target location 84.

Figure 4:
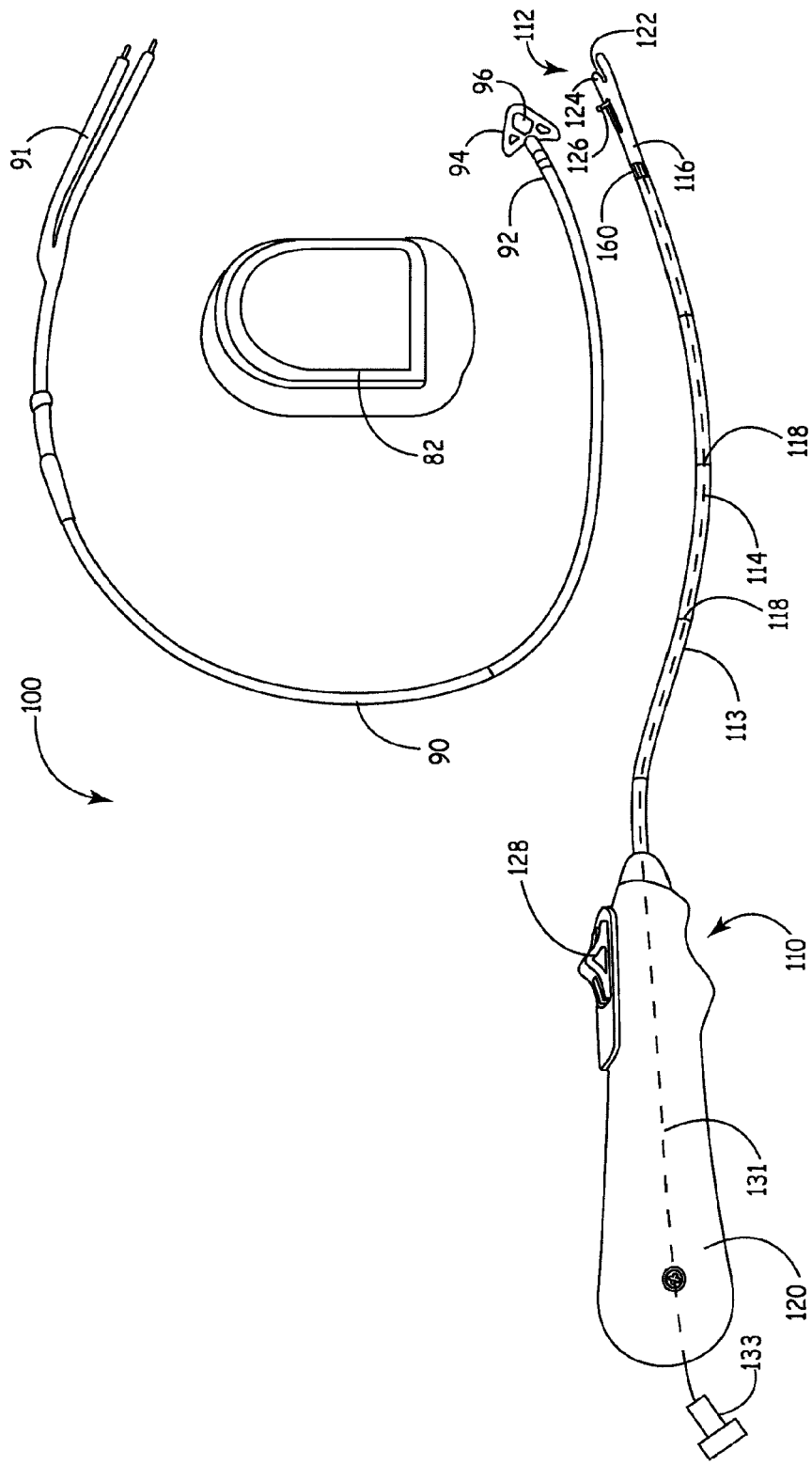
FIG. 4 is a perspective view of an exemplary implantation and tunneling kit including an implantable medical device, a medical lead and a tunneling tool.

Referring to FIG. 4, an exemplary implantation and tunneling kit 100 that can be used with the subcutaneous lead delivery method according to the present teachings can include an implantable device 82, an electrical lead 90, and a tunneling tool 110. The lead 90 and the tunneling tool 110 can be, for example, similar to those disclosed in U.S. Patent Publication Nos. 2008/0208339, 2008/0208303, 2008/0208248, and 2008/0208247, each to Rutten et al., or U.S. patent application Ser. No. 12/250,670 to Wengreen et al., each of which is incorporated by reference herein in its entirety. The tunneling tool 110 can be used to form a subcutaneous tunnel within a patient 14 for passage of the electrical lead 90, as described below. It should be appreciated, however that other tunneling tools and methods can be used to form the tunnel and deliver the lead, as discussed below.

Figure 5:
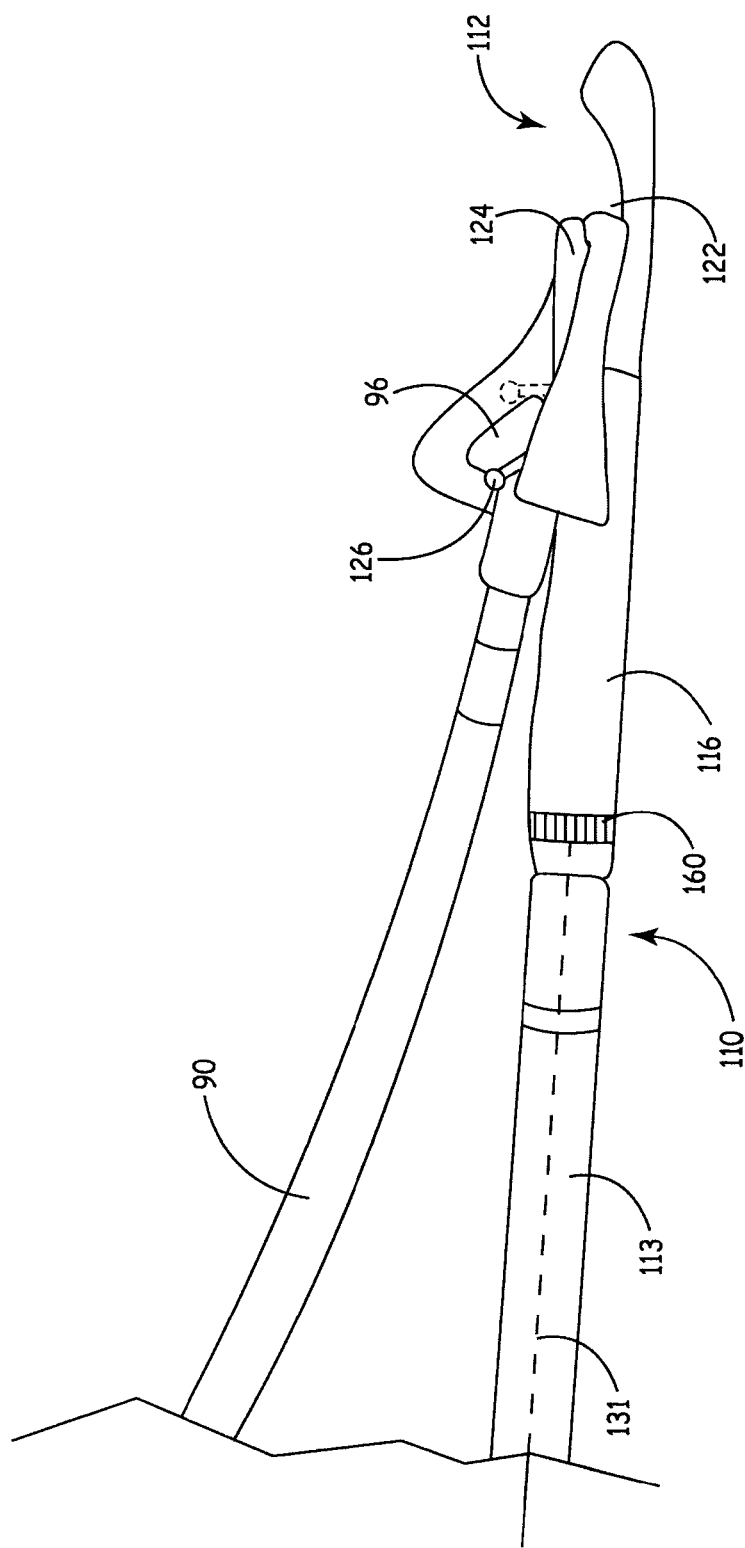
FIG. 5 is a detail of coupling the medical lead to the tunneling tool of the implantation and tunneling kit of FIG. 4.

Referring to FIGS. 4 and 5, the lead 90 can include a connector 91 at proximal end for connection with the implantable device 82 and a fixation member 94 at a distal end 92. The fixation member 94 can be generally triangular in shape and can be made of resilient, polymeric material, such as, for example, medical grade silicone rubber. The fixation member 94 can include an opening 96 for coupling to a distal or leading end 112 of the tunneling tool 110. The tunneling tool 110 can include a main body 113, which can be, for example, an elongated member having a flexible first portion 114, and a relatively rigid second portion 116 immediately adjacent to the distal end 112. The tunneling tool 110 can include a plurality of length indicators 118, such as bands at predetermined length intervals along the length of the main body 113. The indicators 118 can provide the user with a general indication of how far the main body 113 has been inserted into the patient's body.

The tunneling tool 110 can also include an ergonomic handle 120 for grasping the tunneling tool 110 and advancing the leading end 112 through the patient's body, while forming a subcutaneous tunnel or passage. The leading end 112 can be rounded and can include a curved slot 122 forming a hook extension 124. The hook extension 124 can be inserted through the opening 96 of the fixation member 94, such that the fixation member 94 engages and is supported in the slot 122 of the tunneling tool 110.

The tunneling tool 110 can include a securing member 126 movable relative to leading end 112 of the tunneling tool 110. The securing member 126 can move in a direction generally parallel to the axis of the main body 113 between a first or distal position (shown in phantom in FIG. 5) and a second or proximal position (shown in solid lines in FIG. 5) by manipulating an actuator button or slider 128 in the handle 120 of the tunneling tool 110. The actuator button 128 can be operatively coupled to the securing member 126 via a flexible member, such as a cable or string (not shown) that extends through the main body 113 for selectively moving the securing member 126 between the first and second positions. The securing member 126 is received in the opening 96 of the fixation member 9 in the first position. The user can manipulate the actuator button 128 to pull the securing member away from the first/distal position and toward the second/proximal position (shown in solid lines in FIG. 5). As a result, the resilient fixation member 94 can be stretched between the securing member 126 and the hook extension 124 securing the lead 90 to the tunneling tool 110.

Once the lead 90 is attached to the tunneling tool 110, the leading end 112 of the tunneling tool 110 with the attached lead 90 can be inserted into a prepared incision 80 (or other incision) in the patient 14. The leading end 112 can be advanced toward a posterior area of the patient 14, such as toward the middle spine. As the leading end 112 advances within the patient 14, the leading end 112 separates the patient's skin from the patient's muscle and/or fat, creating a subcutaneous tunnel. Simultaneously, as the leading end 112 advances, the tunneling tool 110 pulls and advances the lead 90 within the tunnel. The tunneling tool can include one or more position sensors 160 on the distal rigid portion 116 of the tunneling tool 110 for tracking the tunneling tool in navigation system. The position sensors 160 can be electrically coupled to a cable 131, which passes through the main body 113 and the handle 120 of the tunneling tool 110 and has a connector 133 at its proximal end. The connector 133 can operationally connected to a navigation probe interface, such as the navigation probe interface 50 of the navigation system 10 shown in FIG. 1A.

Various devices and methods of accurately guiding the lead 90 subcutaneously without the use of fluoroscopy, such that the lead remains between the skin and muscle/fat tissue are described below in reference to FIGS. 6-14. The non-fluoroscopic guidance utilizes position sensors, such as electromagnetic coils, on a tunneling tool and on a re-usable navigation catheter which is placed outside the patient 14 along a desired path from the incision site to the target site. For example, the electromagnetic catheter 52 of FIG. 1 can be replaced with a tunneling tool 110 illustrated in FIG. 4, and the dynamic reference frame 54 of FIG. 1 can be replaced with the guide strap 130 and navigation catheter 130 illustrated in FIGS. 7B and 12A, as discussed below.

Figure 6:
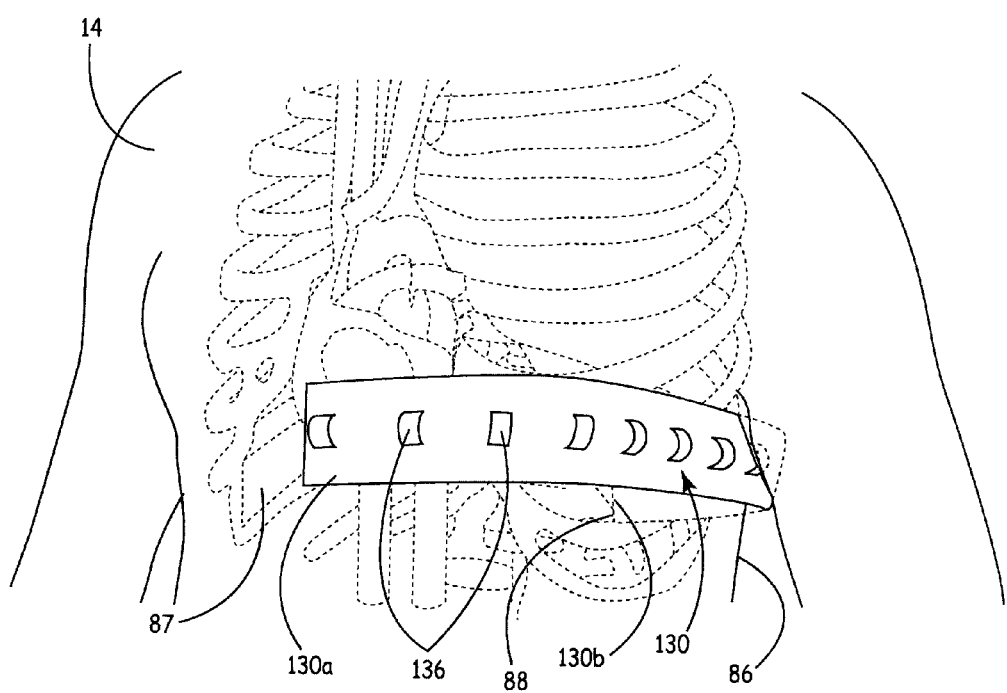
FIG. 6 is an environmental view of a guide strap attached on the skin of a patient from an anterior incision to the posterior target site according to the present teachings.

More specifically, and in various embodiments, as illustrated for example in FIGS. 6-7D, a flexible guide strap 130 can extend between first and second ends 130a, 130b and can be placed externally over the skin surface 86 of the patient 14 between a first location 87 on the skin surface 86 adjacent to the incision 80 to a second location 88 on the skin surface 86 adjacent the target site 84 along a planned tunneling path. The guide strap 130 can include a substrate 132 with a light adhesive for removable attachment to the skin 86 and an upper layer 134 attached to the substrate 132, as illustrated in FIG. 7C. The substrate 132 can be made of medical grade foam or other biocompatible material. The upper layer 134 can be made, for example, from polyester, Mylar or other biocompatible material. The guide strap 130 can be constructed to have sufficient flexibility to follow the contour of skin surface 86 and also sufficient stiffness to keep the skin surface 86 taut for facilitation guidance and steering of the tunneling tool 110. A plurality of retainer formations 136 can be formed on the upper layer 134 of the guide strap 130 for retaining a reference or navigation catheter 150. The retainer formations 136 can be, for example, in the form of hoops or loops, each retainer formation 136 defining a retainer opening 138 through which the navigation catheter 150 can pass.

In various embodiments, the retainer formations can be integrally formed with the guide strap 130. In other embodiments, the retainer formations 136 can be constructed with small pieces of relatively thin adhesive tape attached to the guide strap 130. Additional details, including various materials and embodiments for the guide strap 130 are disclosed in U.S. Provisional Application No. 61/116,492, filed on Nov. 20, 2008, the disclosure of which is incorporated herein by reference.

The navigation catheter 150 can be a flexible and reusable catheter, but similar in other respects to the model 10158 catheter insert, which is an investigational device available to qualified individuals for certain single use applications from Medtronic, Inc., Minneapolis, Minn., or the catheter disclosed in co-pending and commonly assigned US. Patent Publication 2007/0164900, published Jul. 19, 2007, which is incorporated herein by reference. The navigation catheter 150 can include a plurality of position sensors 140, such as, for example, eight to twelve receiver coils electrically coupled with conductor wires for connection with a navigation system, such as the navigation system 10 described above. As can be seen in the illustrations of FIGS. 7C and 7D, when the navigation catheter 150 is operably coupled to the navigation system 10, a subcutaneous navigation volume 170 can be generated in reference to the position sensors 140. The navigation volume 170 provides a visualization of subcutaneous path for the tunneling tool 110, as it moves from the anterior incision 80 to the posterior target site 84. It is noted that the position sensors 140 act as dynamic references that move with patient respiration and patient movement on the table 56. The corresponding navigation volume 170 generated in relation to the position sensors 140 is also dynamic and moves similarly in response to patient respiration or movement. In this respect the guide strap 130 with navigation catheter 150 can provide a dynamic reference frame 54 with six degrees of freedom.

Referring to FIGS. 7B-8C, a coordinate system illustrating a sagittal plane SP, a frontal or coronal plane FP and an axial or transverse plane TP is shown in relation to the guide strap 130. A representative array of position sensors 140 is illustrated diagrammatically with a series of digital representations of the sensors or sensor images 140a. The series of sensor images 140a on the sagittal plane SP is illustrated in FIG. 8A, and in FIG. 8B in relation to the navigation volume 170. These digital images can be loaded on a display 36 associated with the navigation system 10.

The path of the tunneling tool 110 can be visualized on a display 36 of the navigation system, as shown in the screenshots of FIGS. 9A-11B. In these screenshots, the same reference numbers are used for the actual devices and their digital images. In particular, a segment of the rigid distal portion 116, of about 100 mm or so from the most proximal position sensor 160 to the leading end 112 of the tunneling tool 110 can be digitally represented on the display 36 in relation to the navigation volume 170. Referring to FIGS. 9A and 9B, an image or digital representation of the distal portion 116 of the tunneling tool 110 is shown at the entrance portion of the navigation volume 170. In the sectional view of FIG. 9A, as an aid for keeping the leading end 112 of the tunneling tool 110 centered within the navigation volume, a visual indication may be provided. For example, an inner region 174 surrounded by an outer annular band 172 can shown on the display 36 with different colors. The leading end 112 of the tunneling tool can be viewed as a circular region in the inner region 174 of the navigation volume. For better guidance, the leading end 112 can be biased subcutaneously toward the fat tissue rather than the muscle.

Referring to FIGS. 10A and 10B, an exemplary illustration of an instance in which the leading end 112 of the tunneling tool 110 has veered slightly off the navigation volume 170 toward muscle tissue is displayed on the screen on the transverse plane TP (FIG. 10B) and on the sectional view (FIG. 10A). A change in color, such as from green to red or an audible signal can alert the medical professional to correct the trajectory back inside the navigation volume 170, until the leading end 112 of the tunneling tool 110 reaches the target site 84, as shown in FIGS. 11A and 11B. The change in color or other visual or audible alert device can facilitate subcutaneous guidance, because registration between patient space and image space with pre-acquired fluoroscopic or X-ray or other medical images need not be used, according to the present teachings.

The lead 90 can be delivered to the target site by removably coupling to the tunneling tool 110 as described in connection with the exemplary embodiments of the lead and tunneling tool of FIGS. 4 and 5. Optionally, live fluoroscopy can be used if it is desired to verify the final lead position after removing the tunneling tool 110. In various alternative embodiments, a catheter, such as the catheter 52 of the navigation system shown in FIGS. 1 and 1A, can be placed over the tunneling tool 110 and navigated to the target site 84. Then, the tunneling tool 110 can be removed and the lead 90 can be inserted through the catheter 52 to the target site 84.

Figures 12A, 12B:
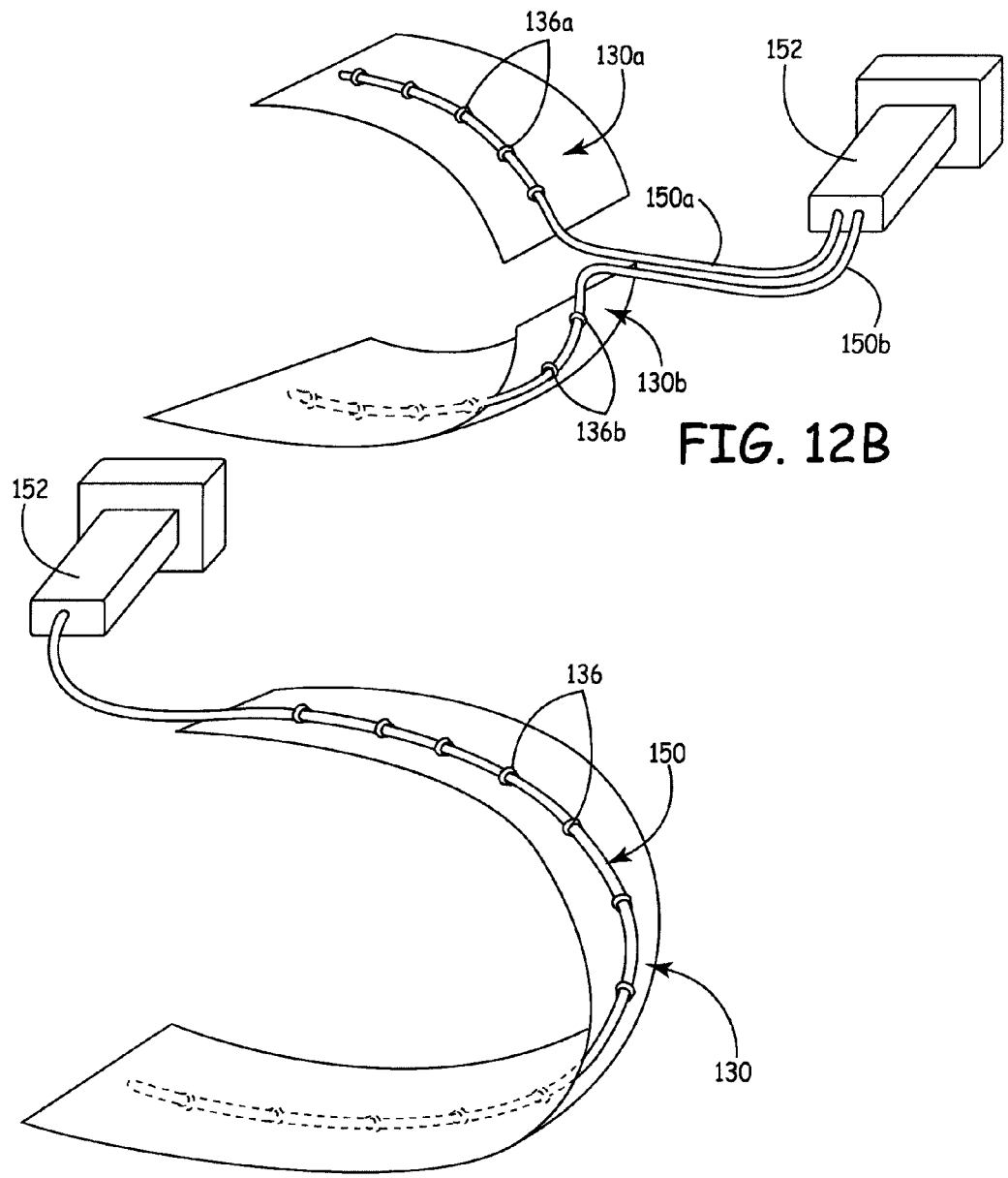
FIG. 12A is a perspective view of a navigation catheter coupled to a guide strap for subcutaneous lead delivery according to the present teachings.
FIG. 12B is a perspective view of two navigation catheters coupled to corresponding guide straps for subcutaneous lead delivery according to the present teachings.

Referring to FIG. 12A, the navigation catheter 150 is shown with the guide strap 130, as discussed above, and a connector 152 for operatively coupling to the navigation system 10. Referring to FIG. 12B, first and second navigation catheters 150a 150b are illustrated with corresponding first and second guide straps 130a, 130b each passing through a plurality of retainer formations 136a and 136b of guides straps 130a, 130b (as previously described in conjunction with FIG. 11A) for use with a two-step procedure in which a second incision to lateral thorax is used to tunnel to the first or pectoral incision 80 and to the posterior target site 84.

Figure 13:
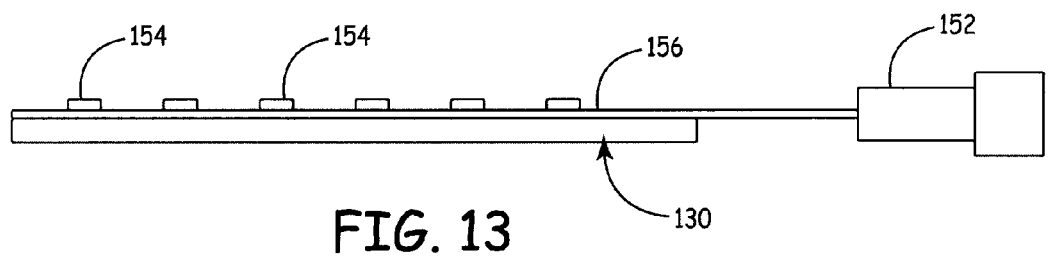
FIG. 13 is a side view of a guide strap with a shielded flexible circuit for connection with a navigation system for subcutaneous lead delivery according to the present teachings.

In various alternative embodiments, instead of the navigation catheter 150, a shielded flexible circuit 156 with position sensors, such as, for example, induction coils 154 can be attached to the guide strap 130 and coupled to the navigation system 10 via a connector 152, as shown in FIG. 13. Induction coils 156 with flip chip technology can be used, or alternatively, thin film coil sensors. The shielded flex circuit 156 with the guide strap 130 can be used in a similar manner as described above in connection with FIGS. 3-12B for guiding the tunneling tool 110 subcutaneously without fluoroscopic imaging. A three-dimensional dynamic reference frame 54 can be integrated with the flexible circuit 156 and guide strap 130 by providing an arrangement of two orthogonal coils 154, at least at one position.

Figure 14:
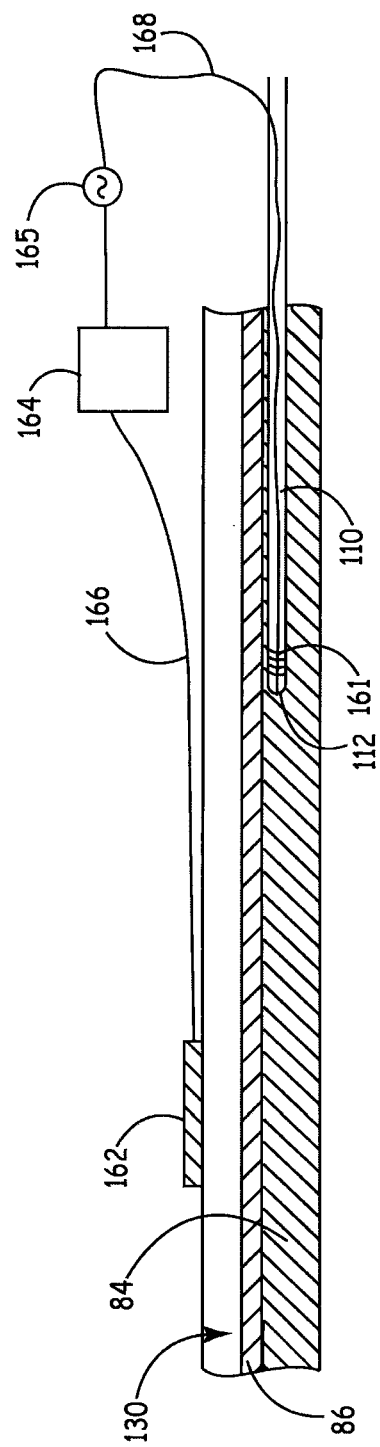
FIG. 14 is an environmental sectional view of an impedance feedback system for subcutaneous lead delivery system according to the present teachings.

Referring to FIG. 14, in various alternative embodiments, an impedance feedback device 164 can be used to guide the tunneling tool 110. The guide strap 130 can be attached on the skin 86 of the patient along the path to be followed by the tunneling tool 110. The tunneling tool 110 can include a first electrode 161 adjacent the leading end 112 of the tunneling tool 110. The electrode 161 can be electrically coupled to the impedance feedback device 164 via a first electrical wire or cable 168. At least one second electrode 162 can be placed over the guide strap 130 above the target site 84 or alternatively a plurality of electrodes 162 can be placed along the entire length of the guide strap 130. The second electrode 162 can be electrically coupled via a second electrical wire or cable 166 with the impedance feedback device 164. The impedance feedback device 164 can measure the impedance along the wire path from the second electrode 162 above the target site 84 to the first electrode 161 at the leading end 112 of the tunneling tool 110 and provide an alert signal or a feedback varying with resistance in the form of an audio signal or a visual signal. For example, as the leading end 112 of the tunneling tool 110 approaches the target site 84, the tone of the audio signal can change to a lower frequency, or the visual signal can change color from a red hue to a green hue. Similarly, if the leading end 112 of the tunneling tool 110 strays or veers off a path defined by the plurality of electrodes 162 on the guide strap, a different tone or visual indication alert can be provided to the medical professional for correcting the path of the tunneling tool. A voltage source 165 can be coupled between the second electrode 162 and the first electrode 161 to activate the electrical circuit. The tunneling tool 110 can be guided to the target site 84 solely under the guidance of the feedback signal without using other navigation aids, i.e., without fluoroscopic imaging and without navigation guidance via a navigation system 10, for example.

As described above, the present teachings provide various embodiments and methods for guiding a tunneling tool subcutaneously and delivering a lead through tissue without the use of fluoroscopic guidance and registration. In contrast to transvenous implantation approaches, in non transvenous or subcutaneous lead delivery and implantation, such as in implantation of ICD or ICM systems, for example, the relative shallow path under tissue presents the opportunity to avoid radiation associated fluoroscopic navigation while providing cost savings and simplicity of use.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An apparatus for subcutaneous lead guidance comprising:
   a flexible guide strap having a first end and a second end, the guide strap adapted to be attachable on a patient's skin to extend along a planned tunneling path between the first end positioned adjacent an incision and the second end positioned adjacent a target site;
   a shielded flexible circuit and a plurality of induction coils attached to the guide strap to define the planned tunneling path from the incision to the target site;
   a tunneling tool having a distal portion with a leading end and at least one position sensor on the distal portion; and
   a feedback device coupled to the tunneling tool and the flexible circuit and configured to generate a first feedback signal as the leading end approaches the target site within the planned tunneling path and a second feedback signal different than the first feedback signal if the leading end veers off the planned tunneling path.

2. The apparatus of claim 1, further comprising a medical lead having a fixation member removably engageable with the leading end of the tunneling tool.

3. The apparatus of claim 1, wherein the generated navigation volume providing the subcutaneous path for the tunneling tool being dynamic in response to patient movement.

4. The apparatus of claim 1, wherein the digital representation of the distal portion in relation to the navigation volume on the display comprises a visual indication of the distal portion relative to an inner region of the navigation volume and an outer annular band of the navigation volume.

5. A method for subcutaneous lead guidance comprising:

attaching a first end of a substrate of a flexible guide strap on a patient's skin adjacent to an incision site and a second end of the substrate over a target site, the guide strap including a shielded flexible circuit with a plurality of induction coils extending between the first end and the second end defining a planned tunneling path from the incision site to the target site;

guiding a tunneling tool subcutaneously through the incision to the target site without fluoroscopic assistance, the tunneling tool having at least one position sensor coupled to a distal portion of the tunneling tool; and enabling a feedback device coupled to the guide strap and the tunneling tool to measure a position signal from the position sensor and the induction coils and in response to the position signal generate a first feedback signal if the position sensor approaches the target site along the planned tunneling path and a second feedback signal different than the first feedback signal if the position sensor veers off the planned tunneling path to assist a user in advancing the leading end to the target site.

6. The method of claim 5, further comprising:

coupling a distal end of a medical lead to the leading end of the tunneling tool; and guiding the distal end of the medical lead subcutaneously through the incision to the target site.

7. The method of claim 5, wherein the first feedback signal comprises a first audible frequency and the second feedback signal comprises a second audible frequency different than the first audible frequency.

* * * * *